United States Patent [19]

Kunig et al.

[11] Patent Number: 5,370,122
[45] Date of Patent: Dec. 6, 1994

[54] METHOD AND APPARATUS FOR MEASURING MYOCARDIAL IMPAIRMENT, DYSFUNCTIONS, SUFFICIENCY, AND INSUFFICIENCY

[76] Inventors: Horst E. Kunig; Sabine V. Kunig, both of P.O. Box 192, Saltsburg, Pa. 15681

[21] Appl. No.: 133,565

[22] Filed: Oct. 8, 1993

Related U.S. Application Data

[63] Continuation-in-part of Ser. No. 112,443, Aug. 26, 1993, which is a continuation-in-part of Ser. No. 978,108, Nov. 18, 1992, abandoned.

[51] Int. Cl.$^5$ .............................................. A61B 5/029
[52] U.S. Cl. ..................................... 128/670; 128/713; 128/668; 128/694
[58] Field of Search ............................. 128/691–692, 128/694, 713, 736, 670–671, 672, 668

[56] References Cited

U.S. PATENT DOCUMENTS

4,632,125 12/1986 Webler et al. .................. 128/692
4,877,035 10/1989 Bogen et al. .................... 128/673
5,046,502 9/1991 Kunig ............................. 128/670

Primary Examiner—Angela D. Sykes
Attorney, Agent, or Firm—Clifford A. Poff

[57] ABSTRACT

A monitoring device for cardiac efficiency and cardiac sufficiency derived from pre-ejection and post-ejection potentials, cardiac metabolic rate, and cardiac power receives signals representative of ventricular pressures and sizes, body temperature, age, and sex. Cardiac efficiency is determined as the ratio of the mechanical work of the heart performed in one cardiac cycle which is equal to the difference of pre-ejection potential and post-ejection potential to the highest pre-ejection potential. Metabolic rate is determined as a multiple of the minimum cardiac work necessary to sustain life. Cardiac power is determined as the ratio of cardiac work to the time in which this work is performed. Cardiac efficiency and cardiac power are used to determine myocardial impairment, dysfunctions, sufficiency, and insufficiency.

22 Claims, 5 Drawing Sheets

METHOD AND APPARATUS FOR MEASURING MYOCARDIAL IMPAIRMENT, DYSFUNCTIONS, SUFFICIENCY, AND INSUFFICIENCY

CROSS REFERENCE TO RELATED APPLICATION

This application is a continuation-in-part of U.S. patent application Ser. No. 08/112,443, Filed Aug. 26, 1993, pending, which is a continuation-in-part of U.S. patent application Ser. No. 07/978,108, Filed Nov. 18, 1992, now abandoned.

BACKGROUND OF THE INVENTION

1. Field of the Invention

The present invention relates to a cardiac monitor and, specifically to methods and apparatus using detectors and measurements provided thereby of cardiac functions for determining ventricular pressure-size curves, pre-ejection potentials, post-ejection potentials, cardiac efficiency, cardiac metabolic rate, cardiac power, pre-ejection power, and contractility for comparison with preestablished levels to allow diagnosis and monitoring of myocardial impairment, dysfunction, sufficiency, and insufficiency of an individual.

2. Description of the Prior Art

Presently, hemodynamics measures a multiplicity of parameters and compares them against an empirically established norm. As disclosed in 1978 by Yang, et al. in a work entitled *From Cardiac Catheterization Data to Hemodynamic Parameters*, published by F. A. Davis Co., Philadelphia, Pa. 1978, a heart rate of between 60 and 100 beats per minute and a blood pressure of 120/80 mm Hg are considered normal. Also, a cardiac output, CO, of 5 l/min is considered to be normal. Yet, CO may have a normal numeral value computed according to $CO = SV * HR$ as, for example, may be the result of an abnormal stroke volume, SV, of 42 ml which is compensated by an abnormally high heart rate, HR, of 120 l/sec. Furthermore, a stroke volume of 70 ml, considered to be normal, may be caused by an abnormal end-diastolic volume, EDV, of 270 ml and an abnormal end-systolic volume, ESV, of 200 ml, when computed according to $SV = EDV - ESV$. Therapies are subjectively developed based on physicians' experience to correct one or more hemodynamic outliers to return to the normal range.

In contrast to hemodynamics, the present invention utilizes actual measurements of cardiac functions for diagnosing efficiency and cardiac power to assess the performance of the heart as a working system and objectively develop therapies to cause the heart to work efficiently and sufficiently based on ventricular pressure-size curves.

It is therefore an object of the present invention to diagnose a cardiac condition of a subject by obtaining select measurements of cardiac functions for determining the present ventricular pressure-size curves and the present working efficiency represented thereby of the heart as a pump in the circulatory system and comparing such present ventricular pressure-size curves and present working efficiency with pre-determined reference pressure-size curves and working efficiency representing a normal subject at rest.

It is another object of the present invention to determine present pre-ejection potential using cardiac measurements of cardiac functions, pre-ejection potentials and post-ejection potentials indicative of the manner in which a subject performs cardiac work and comparing the subject's pre-ejection potentials and post-ejection potentials with pre-determined reference pre-ejection and post-ejection potentials of a normal with deviations thereof being an indicator of improper cardiac functions.

It is still another object of the present invention to determine present sufficiency of the heart using measurements of cardiac functions in terms of cardiac power and compare the present cardiac power of the subject with the threshold cardiac power needed to sustain life where a deficiency of cardiac power expended indicates an insufficiency or a life-threatening emergency and an excess of cardiac power expended indicates the existence of a dysfunction of the organism.

It is further an object of the present invention to determine whether the dysfunction, represented by an excess of cardiac power requirement is compensated sufficiently, as indicated by high magnitudes of cardiac efficiency, or insufficiently, as indicated by low magnitudes of cardiac efficiency in case of myocardial impairment by the use of measurements of cardiac functions.

It is still another object of the present invention to determine maximum pre-ejection power the heart must attain and the fraction thereof which the heart must expend to sustain life and overcome a dysfunction.

It is furthermore an object of the present invention to provide a method and apparatus to practice cardiac efficiency and sufficiency diagnostics using measurements of cardiac functions to identify and to monitor therapies which permit the heart to work efficiently and sufficiently.

SUMMARY OF THE PRESENT INVENTION

According to the present invention there is provided a cardiac diagnostic and monitoring device for determining myocardial impairment, dysfunction, sufficiency, and insufficiency of an individual including the combination of a means for producing signals representative of a measure of end-systolic size, end-diastolic size, systolic blood pressure, and diastolic blood pressure of the individual, means responsive to said signals for producing ventricular size and pressure signals representative of cardiac ventricular sizes and ventricular pressures of the individual, means responsive to the ventricular size and pressure signals for producing ventricular pressure-size curves, and means to display the ventricular pressure size curves simultaneously with pre-established curves of a pre-determined reference to allow diagnosis and monitoring of the individual. A pathological state is therefore indicated by incongruent and displaced ventricular pressure-size curves or parts thereof to the pre-established values of normals.

According to another aspect of the present invention there is provided a cardiac diagnostic and monitoring device for an individual including the combination of measuring means producing heart rate, ventricular size, and pressure signals of the individual representative of a measure of cardiac ventricular sizes and ventricular pressures, means responsive to the ventricular size and pressure signals for generating signals representative of energy levels representing pre-ejecting potential and post-ejection potentials of the individual, cardiac ventricular sizes and ventricular pressures of the individual, and display means for simultaneous display of the present energy levels representing pre-ejecting and post-ejection potentials to allow comparison with pre-established energy levels of pre-ejection and post-ejection potentials of a pre-determined reference to allow diagnosis and monitoring of the individual where deviations from the pre-determined reference values indicate a pathological state.

According to a further aspect of the present invention there is provided a method of diagnosing cardiac efficiency, metabolic rate and cardiac power comprising the steps of providing an individual with detectors responsive to cardiac functions by generating ventricular pressure and size signals representing end-diastolic size, end-systolic size, end-diastolic pressure, systolic pressure, of the individual, using the ventricular pressure and size signals to establish ventricular pressure-size curves and pre-ejection and post-ejection potentials of the individual, determining the ventricular pressure-size curve and an energy level of pre-ejection and post-ejection potentials with cardiac basal metabolic rate, and comparing the ventricular pressure-size curves and the pre-ejection and post-ejection potentials of the individual with the respective ventricular pressure-size curve and energy levels of the pre-ejection and post-ejection potentials of a pre-determined reference to assess cardiac efficiency.

The present invention further provides a method for diagnosing cardiac efficiency, metabolic rate, cardiac power, maximal pre-ejection power, and contractility by the steps of providing an individual with detectors responsive to cardiac functions to generate ventricular pressure and size signals representing end-diastolic size, end-systolic size, end-diastolic pressure, systolic pressure, heart rate, and time for completion of one cardiac cycle, using the signals to establish ventricular pressure-size curves, pre-ejection and post-ejection potentials, mechanical work, cardiac metabolic rate, cardiac efficiency, cardiac power, maximal pre-ejection power, and contractility, determining the pressure-size curve with cardiac basal metabolic rate, and the respective pre-ejection and post-ejection potentials, the respective mechanical work being the cardiac basal metabolic rate, measured as 1 CMET, and further using the signals to compare the ventricular pressure-size curves and the pre-ejection and post-ejection potentials with the ventricular pressure-size curve of basal cardiac metabolic rate, and the respective pre-ejection and post-ejection potentials, still further using the signals to determine the cardiac metabolic rate as a multiple of the cardiac basal metabolic rate and the cardiac efficiency and contractility and all hemodynamic parameters standardized with respect to the cardiac metabolic rate.

BRIEF DESCRIPTION OF THE DRAWINGS

The present invention will be more fully understood when the following detailed description is read in light of the accompanying drawings in which.

DETAILED DESCRIPTION OF THE PREFERRED EMBODIMENTS

According to the present invention a cardiac diagnostic and monitoring device is provided for determining ventricular pressure-size curves, pre-ejection potentials, post-ejection potentials, cardiac efficiency, cardiac metabolic rate, and cardiac power, maximal pre-ejection power, and contractility. The device includes means responsive to cardiac functioning for establishing a measure corresponding to ventricular pressures, ventricular sizes, heart rate, time for completion of one heart beat. The device also includes means responsive to the measure of cardiac function for generating pre-ejection potential signals, post-ejection potential signals, cardiac efficiency signals, and cardiac power signals from the ventricular signals and the time interval measurements.

Figure 1A:
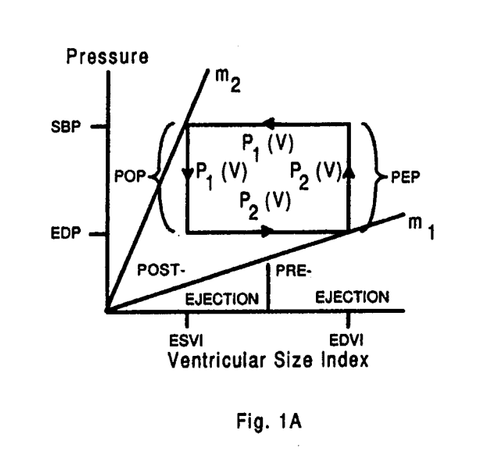
FIG. 1A illustrates a ventricular pressure-size curve for one cardiac cycle.

Referring now particularly to FIG. 1A there is illustrated the ventricular pressure-size curve indicating the changes of ventricular sizes and pressures during a cardiac cycle. It is well understood by those skilled in the art that ventricular volume or ventricular cross-sectional area are representative of ventricular size. Prior to the influx of blood the ventricle attains the end-systolic size ESV and the end-diastolic pressure EDP. After influx of blood the ventricular size increases and attains the end-diastolic size EDV whereupon the pressure also rises to attain the systolic pressure SBP. Subsequently the blood exits the ventricle causing the ventricular size and the ventricular pressure to decrease to the pre-filling state of ESV and EDP, thus, completing one cardiac cycle. A pulmonary artery ejection fraction catheter and/or echocardiographic machinery is used to obtain the ventricular size and ventricular pressure of the heart. The ventricular pressure is obtained by the pressure of blood acting on a membrane sealing an enclosed volume of fluid which in turn acts upon a transducer to provide an electrical signal corresponding to the blood pressure on the membrane. The catheter is also used to obtain the ventricular size by conducting a measured quantity of cold bolus and a thermistor resident in the catheter tip to establish the temperature restoration time during subsequent cardiac cycles. The ventricular sizes of either the left ventricle or right ventricle or both ventricles may be normalized to body surface area (BSA) and are denoted in FIG. 1A as size indices EDVI and ESVI.

The area circumscribed by the ventricular pressure-size trajectory equates with stroke work (W) of the heart according to Yang et al. in a work entitled *From Cardiac Catheterization Data to Hemodynamic Parameters* and published by F. A. Davis Co., Philadelphia, Pa., 1978. The stroke work may be written as $$P*dV = \int_{EDVI}^{ESVI} P_1*dV - \int_{ESVI}^{EDVI} P_2*dV \quad (1)$$

or to perform work the heart must first attain a state of high energy which is defined as pre-ejection potential (PEP)

$$PEP = \int_{EDVI}^{ESVI} P_1*dV \quad (2)$$

then proceed to a state of lower energy defined as post-ejection potential (POP)

$$POP = \int_{ESVI}^{EDVI} P_2*dV \quad (3)$$

where the difference of PEP and POP is converted to stroke work. If the area under the pressure-size trajectory is approximated by a rectangle, then equation (1) simplifies to:

$$W=(EDVI-ESVI)*(SBP-EDP) \quad (4)$$

Multiplication of the two factors in equation (4) and rewriting the terms yields:

$$W=(EDVI*SBP-EDVI*EDP)-(ESVI*SBP-ESVI*EDP) \text{ or } W=PEP-POP \quad (5)$$

where;

$$PEP=EDVI*SBP-EDVI*EDP \quad (6)$$

and $$POP=ESVI*SBP-ESVI*EDP. \quad (7)$$

Using the abbreviations $PEP_{max}=EDVI*SBP$; $PEP_{min}=EDVI*EDP$; $POP_{max}=ESVI*SBP$; and $POP_{min}=ESVI*EDP$; the pre-ejection potential equation (6) and the post-ejection potential equation (7) may be written as:

$$PEP=PEP_{max}-PEP_{min} \quad (8)$$

and $$POP=POP_{max}-POP_{min} \quad (9)$$

where $PEP_{max}$ is the upper limit of PEP; $PEP_{min}$ is the lower limit of PEP; $POP_{max}$ is the upper limit of POP; and $POP_{min}$ is the lower limit of POP.

Figure 1B:
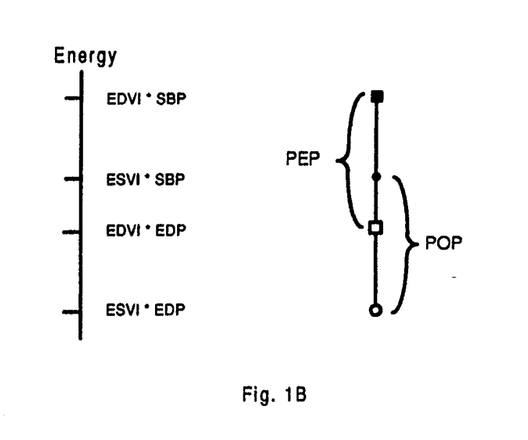
FIG. 1B illustrates plot points in an energy scale for pre-ejection potentials and the post-ejection potentials derived according to the present invention.

Referring now particularly to FIG. 1B, the mechanical work is the difference between two potentials, namely the pre-ejection potential (PEP) and the post-ejection potential (POP), where each potential, being represented by a difference of two energy states $PEP_{max}-PEP_{min}$ and $POP_{max}-POP_{min}$ or an energy band. By adjusting the upper and lower limits of PEP and POP and the difference between PEP and POP, the heart is flexible to perform the specific work to accommodate the instantaneous circulatory needs. Equation (5) demonstrates that PEP and POP uniquely determine W, However, equal magnitudes of W may be obtained by a multiplicity of $PEP_{max}$, $PEP_{min}$ and $POP_{max}$, $POP_{min}$ arrangements. Deviations of $PEP_{max}$, $PEP_{min}$ and $POP_{max}$, $POP_{min}$ for a subject from pre-determined values representative of a normal indicates a pathological cardiac state despite equal magnitudes of cardiac work performed by the normal and the pathological heart. PEP and POP may also be thought of as preload and afterload.

The efficiency of a system is determined by the ratio of the work performed in relation to the energy expended. Accordingly, cardiac efficiency (CF) is determined as:

$$CF=W/EDVI*SBP=(PEP-POP)/EDVI*SBP \quad (10)$$

with EDVI * SBP being the upper limit of the pre-ejection potential. Using equations (6), (7), and (10), if EDP=0 or ESVI=0, then CF=(EDVI−ESVI)/EDVI or (SBP−EDP)/SBP, respectively. These two equation may be recognized as representing the (volume) ejection fraction, EF(V), and, in analogy, the (pressure) ejection fraction, EF(P). Inserting values for normals at rest as reported by Yang et al. in a work entitled *From Cardiac Catheterization Data to Hemodynamic Parameters*, published by F. A. Davis Co., Philadelphia, Pa. 1978 and in *Geigy Scientific Tables*, Volume 5, Ciba-Geigy Corporation, West Caldwell, N.J. 07006, 1990, into equation (10) yields cardiac efficiency for the right heart CF=30% and for the left heart CF=50%. A myocardial impairment exists if CF<30% and CF<50% for the right and left hearts, respectively. The smaller CF, the greater is the myocardial impairment. The CF scale, therefore, is a quantitative measure to diagnose myocardial impairment. According to the present invention an apparatus and a method are disclosed to diagnose myocardial impairment by determining the present cardiac efficiency of a subject and comparing said efficiency with a pre-determined cardiac efficiency of a normal using the CF scale.

For EDP=ESVI=0, CF=100%. In general, smaller EDP and ESVI values produce larger CF values. As a corollary, the hearts of children with small ventricular volumes may not pump as much blood as the hearts of adults, however, the hearts of children work more efficiently. Ventricular sizes and pressures tend to increase with age resulting in decreased efficiency. Also, since the ventricle does not totally collapse after expulsion of blood, that is, ESVI>0, then CF<100%. An apparatus in the form of a two dimensional visual display is provided to indicate the displacement of the ventricular pressure-size curve of a myocardial impaired subject and to identify which parameters need be changed to normalize cardiac efficiency.

The work (W) performed during the time of one heart beat (RR) is defined as cardiac power (CP). It may be expressed as:

$$CP=W/RR=(PEP-POP)/RR \quad (11)$$

Solving equation (10) for W and replacing W in equation (11) yields:

$$CP=CF*(EDVI*SBP/RR) \quad (12)$$

which states that the expended cardiac power, CP, is a fraction, CF, of a maximal cardiac power, EDVI * SBP/RR. More CP must be expended if a subject exercises in comparison to when a subject is at rest. Conversely, if an excessive CP is expended when the subject is at rest then the excessive CP cannot be caused by exercise. Instead, the excessive CP is a result of a dysfunction of the organism where the heart expends the excessive power to compensate the dysfunction. Inserting values for normals at rest as reported by Yang et al. in a work entitled *From Cardiac Catheterization to Hemodynamic Parameters*, published by F. A. Davis Co., Philadelphia, Pa. 1978 and in *Geigy Scientific Tables*, Volume 5, Ciba-Geigy Corporation, West Caldwell, N.J. 07006, 1990 into equation (11) yields cardiac power for the right heart $CP=0.71 * 10^6$ erg/m$^2$*sec and for the left ventricular heart in terms of volume $CP=5.65 * 10^6$ erg/m$^2$* sec, and in terms of cross-sectional area $CP=625$ (cm$^2$/m$^2$) * mm Hg. These cardiac powers are the minimum cardiac powers the respective ventricles must expend to sustain life and is, therefore, the basal cardiac metabolic rate for which a unit measure of 1 CMET/sec is introduced. Dysfunctions, defined by an excessive CP expenditure, are measured as a multiple of 1 CMET/sec. The greater the intensity of a dysfunction, the greater is the cardiac power requirement and the greater multiple of CMET/sec is measured.

Figure 2:
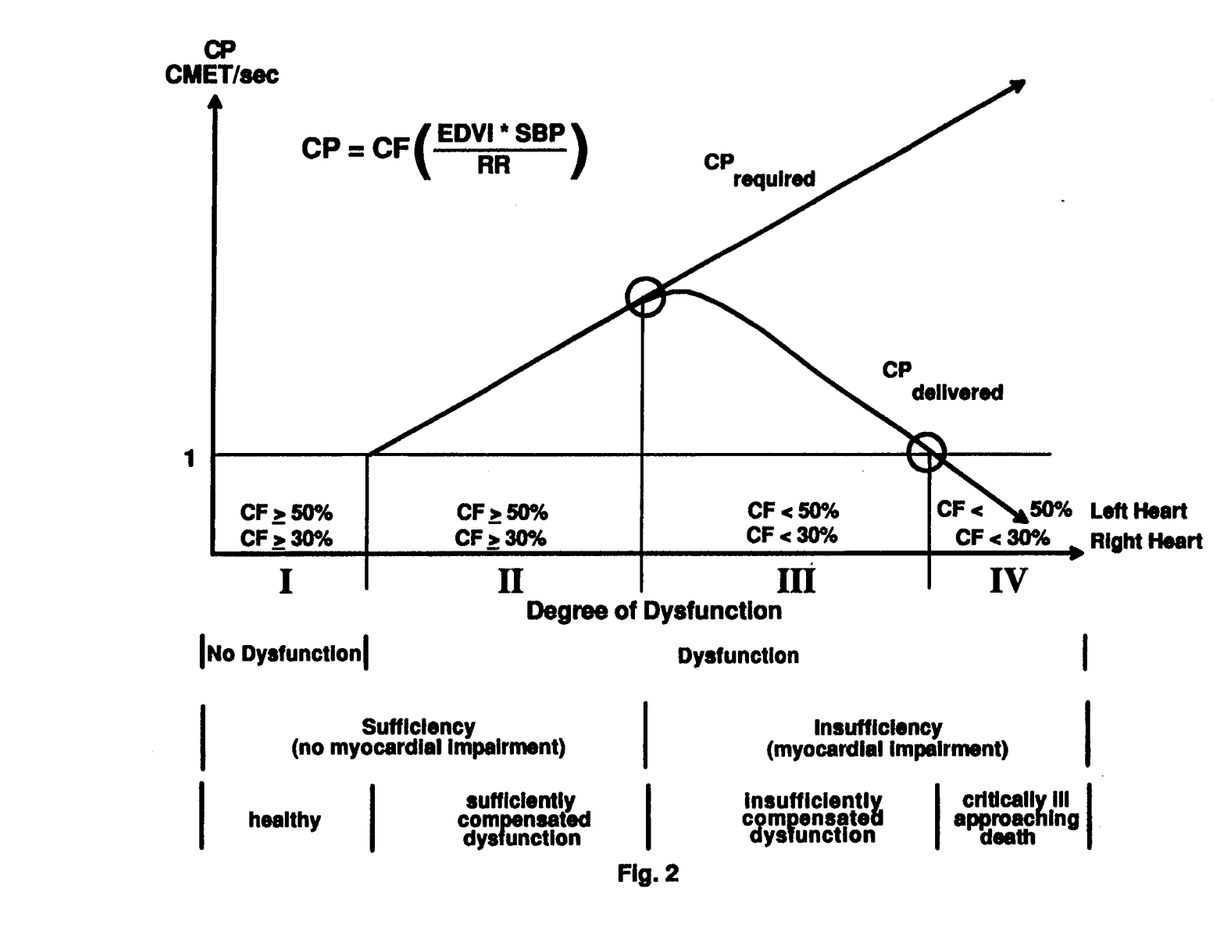
FIG. 2 illustrates graphically the myocardial impairment, dysfunction, sufficiency, and insufficiency through the use of cardiac measuring and computation according to the present invention.

Referring now to FIG. 2 cardiac power, CP, is plotted versus the degree of the dysfunction for determination of sufficiency and insufficiency. If measurements are taken at rest, no dysfunction exists, if $CP=1$ CMET/sec, quadrant I. However, by definition, a dysfunction appears if $CP>1$ CMET/sec. Also, the greater the intensity of the dysfunction, the greater the required CP expenditure, $CP_{required}$, quadrants II through IV. Initially, the heart may satisfy the CP requirement by delivering an equal magnitude CP such that $CP_{delivered}=CP_{required}$, quadrant II. In this case CP is delivered to compensate the dysfunction and, therefore, sufficiency is defined as the case where $CP_{delivered}=CP_{required}$, quadrants I and II. According to equation (12), the heart may satisfy increased CP requirements by working more efficiently (increased CF) or by attaining higher maximal cardiac power values (increased EDVI * SBP/RR). However, there exist physiologically imposed upper limits for cardiac efficiency and maximal cardiac power. If $CP_{required}$ exceeds $CP_{delivered}$, quadrants III and IV, then $CP_{delivered}$ compensates the dysfunction insufficiently. In this case, $CP_{delivered}<CP_{required}$, the dysfunction converts to an insufficiency. Finally, $CP_{delivered}<1$ CMET/sec in the presence of an insufficiency, quadrant IV, means that not enough cardiac power is delivered to sustain life. Death is imminent for this critically ill patient. Equation (12) is also used for the determination whether the dysfunction is sufficiently or insufficiently compensated. A right heart without a myocardial impairment, $CF\geq30\%$ and a left heart without myocardial impairment, $CF\geq50\%$ is needed to satisfy the condition for sufficiency, $CP_{delivered}=CP_{required}$. Conversely, $CF<30\%$ and $CF<50\%$, respectively, according to equation (12), reduces $CP_{delivered}$. As a result, $CP_{delivered}<CP_{required}$, which is the condition for insufficiency. Thus an insufficiency exists for $CF<30\%$. According to the present invention an apparatus is disclosed to select pre-determined ventricular pressure-size curves with $CF=30\%$ (right heart), $CF=50\%$ (left heart), and $CP=1$ CMET/sec and to compare present ventricular pressure-size curves of a subject with the pre-determined ventricular pressure-size curves to diagnose myocardial impairment, and/or sufficiently or insufficiently compensated dysfunctions of the organism as measured on the CF and CP scale using the following schematic:

1. determination of CF at rest:
   a. $CF<30\%$ and $CF<50\%$ for left and right heart, respectively: existence of a myocardial impairment or insufficiency.
   b. $CF\geq30\%$ and $CF<50\%$ for left and right heart, respectively: no myocardial impairment, sufficiency.
2. determination of CP at rest:
   a. $CF\geq30\%$ and $CF<50\%$ for left and right heart, respectively, and $CP=1$ CMET/sec, quadrant I: sufficiency, no dysfunction, healthy subject.
   b. $CF\geq30\%$ and $CF<50\%$ for left and right heart, respectively, and $CP>1$ CMET/sec, quadrant II: no myocardial impairment, existence of a sufficiently compensated dysfunction.
   c. $CF<30\%$ and $CF<50\%$ for left and right heart, respectively, and $CP\geq1$ CMET/sec, quadrant III: myocardial impairment, existence of an insufficiently compensated dysfunction.
   d. $CF<30\%$ and $CF<50\%$ for left and right heart, respectively, and $CP<1$ CMET/sec, quadrant IV: life cannot be sustained, critical illness, imminent death.

Referring to equation (12), an insufficiently compensated dysfunction a low $CP_{delivered}$ may be increased by either increasing CF, or maximal cardiac power, or both, thus providing either myocardial support, or support to minimize the dysfunction or both. According to the present invention, an apparatus is disclosed for differential diagnosis of the degree of myocardial impairment and dysfunctions by determining CF, CP, and maximal cardiac power to design and monitor therapies which alter CF, CP, and maximal cardiac power, and, thus, reduce the pathological state of the subject.

Contractility is defined as the work performed by the heart under a given load according to Sagawa, et al. from an article entitled *Cardiac Contraction and the Pressure-Volume Relationship*, published in 1988 in the University Press, N.Y. Referring to FIG. 1A the slope of the line $m_2$ through the origin of the pressure-size coordinate system and the point having the coordinates (ESVI,SBP) is considered a measure of contractility according to Sagawa. $m_1$ is the slope of the line passing through the origin and a point having the coordinates (EDVI, EDP). Combining equations (4) and (10) yields $$CON=m_2=m_1/(CF+EDP/SBP+ESVI/EDVI-1) \qquad (13)$$

According to the present invention, the measuring of cardiac functioning process by an apparatus enables a diagnosis of contractility of a subject from the slopes $m_1$ and $m_2$ and by determination of the deviation of the present contractility from the contractility of a pre-determined value the degree of pathology of the heart of the subject.

In the preferred embodiment a computer executes a program to determine pre-ejection potential band and post-ejection potential band from ventricular pressure-size curves and to determine cardiac efficiency as the ratio of the difference of pre-ejection potential band and post-ejection potential band to the upper limit of the pre-ejection potential band. Displays are provided to compare the present ventricular pressure-size curve and the present pre-ejection potential and the present post-ejection potential with the respective ventricular pressure-size curve and the pre-ejection potential and the post-ejection potential representing a pre-determined value. This pre-determined value is the basal cardiac metabolic rate of 1 CMET. A determination and display of cardiac power is obtained as the ratio of mechanical work to the time required by the heart to perform the work. The displays are also provided to ascertain myocardial impairments, dysfunctions, sufficiencies, and insufficiencies as deviations of the present ventricular pressure-size curves, CF, and CP from the pre-determined ventricular pressure-size curve, CF, and CP.

Figure 3:
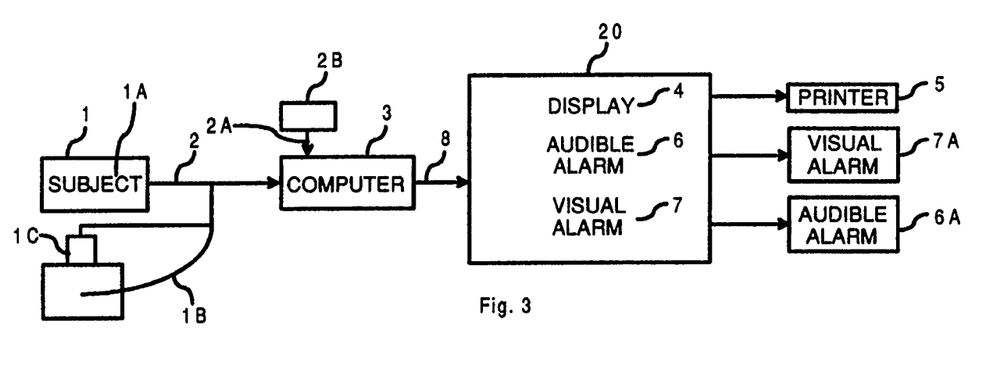
FIG. 3 illustrates a block diagram of circuitry for processing signals according to one embodiment of the present invention.

Referring now to FIG. 3, there is shown a block diagram of the apparatus 10 for practicing cardiac efficiency and sufficiency diagnostics. Signals representative of EDVI, ESVI, SBP, EDP, HR, and RR are derived from subject 1 in a conventional manner and transmitted on a multi wire line 2 as inputs to a computer 3. The subject 1 is implanted with a pulmonary artery ejection fraction catheter 1A. The catheter embodies a known construction for use to generate signals in line 2 representative of systolic and diastolic pulmonary artery pressures, SBP and EDP, respectively, and heart rate (HR). Also, upon injection of a cold bolus via catheter duct 1A signals are generated representative of stroke volume (SV), volume ejection fraction EF(V), end-diastolic volume (EDV) and end-systolic volume (ESV). Alternatively to diagnosis the left heart, there is used a conductance catheter 1B in the left ventricle and an echocardiographic machinery 1C which is used to provide ventricular sized signals. A special purpose catheter can be used in the left ventricle to obtain pressure. The computer 3 also receives input data such as signals representative of height, weight, body surface area (BSA) and subject identification data on line 2A from a source 2B such as a keyboard such as shown in FIG. 3. The computer 3 is programmed with pre-established data signals for comparison with actual signals derived from signals from the subject and processed by the computer 3. The signals processed by the computer 3 are responsive to measurement of ventricular size, ventricular pressure, heart rate, and time to complete one cardiac cycle to determine pre-ejection potentials, post-ejection potentials, cardiac efficiency, cardiac metabolic rate, and cardiac power. Output signals from the computer 3 are applied by line 8 to a monitor 20. The computer 3 processes the input signals to derive new signals representative of pre-ejection potentials, post-ejection potentials, cardiac efficiency, cardiac metabolic rate, and cardiac power and all hemodynamic signals standardized with respect to cardiac metabolic rate. These derived signals are then transmitted on a multi wire line 8 to the monitor 20 which comprises a display 4, an audible alarm 6, a visual alarm 7, and an output for a remote printer 5, a remote audible alarm 6A, a remote visual alarm 7A where the respective signals may be displayed or printed or where they may trigger a remote audible alarm 6A and a remote visual alarm 7A in cases of emergencies when the preset values of the respective signals are not met.

Figure 4:
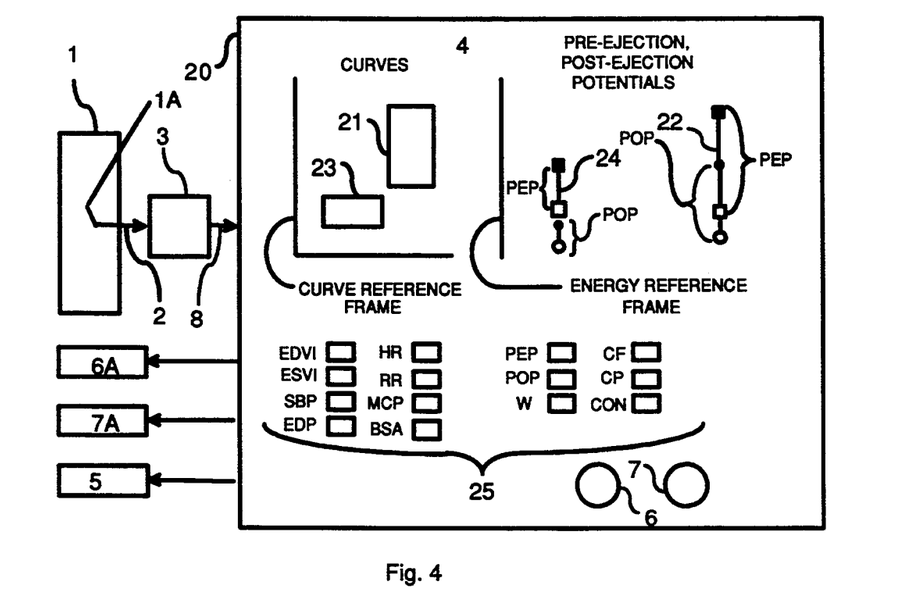
FIG. 4 is a schematic illustration of one embodiment of a display of a monitoring device used to practice the instant invention.
Figure 5:
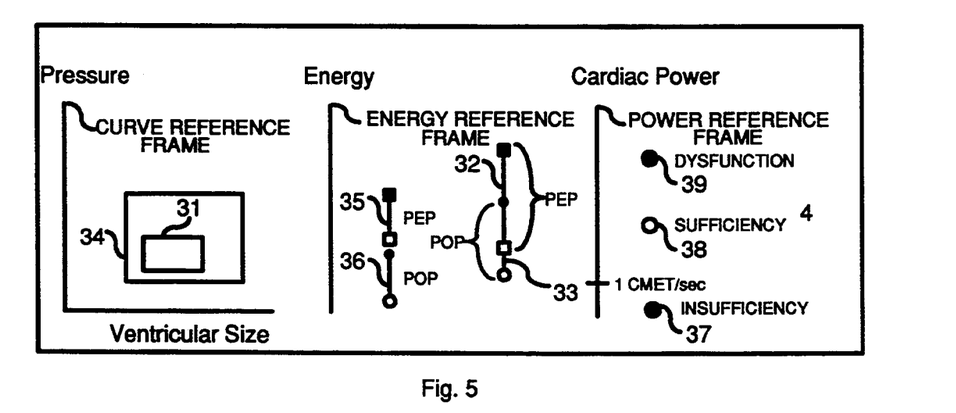
FIG. 5 is an illustration of a second embodiment of a display for diagnostic and monitoring signals according to the present invention.

The teachings of the instant invention are best illustrated in the embodiments as shown in FIGS. 4 and 5. Accordingly, as shown in FIG. 4 there are displayed on the screen display 4 of the cardiac monitor 20 the present ventricular pressure-size curves 21, the present pre-ejection potentials and post-ejection potentials 22 for a patient, the ventricular pressure-size curve 23 with basal cardiac metabolic rate and the pre-ejection potentials and post-ejection potentials 24 derived from the ventricular pressure-size curve 23 representative of normal. Numerical values of hemodynamic parameters EDVI, ESVI, SBP, EDP, HR, RR, BSA, PEP, including the range, lower and upper limits of PEP, POP, including the range, upper and lower limits of POP, CF, W, CP, maximal cardiac power MCP, contractility CON, and the respective data standardized with respect to cardiac metabolic rate are displayed in columns 25. It is further provided that the input data having the greatest impact upon cardiac efficiency and sufficiency of impaired and dysfunctioning hearts flash so as to indicate required changes and easy design of corresponding therapies.

FIG. 4 illustrates the utility of cardiac efficiency and sufficiency diagnosis to judge present ventricular pressure-size curves in relation with the pressure-size curve having cardiac basal metabolic rate as well as present pre-ejection and post-ejection potentials for comparison with pre-ejection and post-ejection potentials derived from the ventricular pressure-size curve of cardiac basal metabolic rate representative of normal. Thus, the computer 3 includes an operation program to construct the displays shown in FIG. 4 useful, for example, to derive therapies to displace present ventricular pressure-size curves with low cardiac efficiency and abnormal PEP/POP arrangements to coincide with the ventricular pressure-size curve and pre-ejection- and post-ejection potentials of cardiac basal metabolic rate. In FIG. 4 there is also shown that the curves 21 and 23 are arranged as a result of the operation of the computer program in a coordinate frame of reference identified by the legend "curve reference frame". Similarly there are also arranged energy levels 22 and 24 as a result of the operation of the computer program in a vertically oriented frame of reference identified by the legend "energy reference frame".

Referring now to FIG. 5 there is differently arranged on the screen 4 of the monitor 20 a display of the present ventricular pressure-size curve 31, present pre-ejection potential 32, and present post-ejection potential 33 of an anesthetized patient and the ventricular pressure-size curve 34, pre-ejection potential 35, and post-ejection potential 36 with basal cardiac metabolic rate of 1 CMET representative of a normal. The present pre-ejection potential 32 and present post-ejection potential 33 and the present ventricular pressure-size curve 31 of the patient appear displaced with respect to the pre-ejection potential 35 and post-ejection potential 36 and the ventricular pressure-size curve 34 of basal cardiac metabolic rate representative of a normal. Furthermore, the area circumscribed by the instant ventricular pressure-size curve 31 is not congruent to the area of the ventricular pressure-volume curve 34 of 1 CMET. The displacement indicates the degree of cardiac dysfunction. Therapies, if they are to benefit the patient, must shift the pre-ejection potential 32 and post-ejection potential 33, and the ventricular pressure-size curve 31 of the patient to coincide with the pre-ejection potential 35 and the post-ejection potential 36 and the ventricular pressure-size curve 34 of cardiac basal metabolic rate. In the instant case EDVI and SBP must be increased and ESVI and EDP must be decreased to obtain larger cardiac efficiency and also to sustain the cardiac basal metabolic rate of 1 CMET and the cardiac power of 1 CMET/sec. The present cardiac power derived from the present pressure volume curve 31 of this subject being less than 1 CMET/sec indicates cardiac insufficiency 37 as indicated on the power reference frame. The ventricular parameters in need of change to obtain higher cardiac efficiency and higher cardiac power to attain sufficiency 38 at CP=1 CMET/sec in case of insufficiency 37 or to obtain a lower cardiac power CP=1 CMET/sec in case of a dysfunction 39 appear flashing on the screen. A summary of data, as published by Grossman in a work entitled *Cardiac Catheterization, Angiography, and Intervention*, Lea and Febiger, Philadelphia, 1991, illustrating cardiac efficiency and sufficiency and dysfunction diagnosis, as it pertains to the right heart, is provided in TABLE 1 where 1 Merg=$10^6$ ergs and 1 CMET=0.71 Merg/m$^2$, N is a normal measured at rest and P 1, P 2, P 3, and P 4 are patients diagnosed as follows:

| | |
|---|---|
| P 1: diagnosis: | mitral regurgitation |
| pressure-volume diagnosis: | CP = 2.5 CMET/sec |
| | CF = 40% |
| | sufficiently compensated dysfunction, no myocardial impairment, quadrant II. |
| P 2: diagnosis: | aortic stenosis |
| pressure-volume diagnosis: | CP = 1.4 CMET/sec |
| | CF = 43% |
| | sufficiently compensated dysfunction, no myocardial impairment, quadrant II. |
| P 3: diagnosis: | aortic stenosis, left ventricular failure |
| pressure-volume diagnosis: | CP = 1.7 CMET/sec |
| | CF = 14% |
| | insufficiently compensated dysfunction, myocardial impairment, quadrant III. |
| P 4: diagnosis: | diabetic with two previous heart attacks |
| pressure-volume diagnosis: | CP = 1.0 CMET/sec |
| | CF = 18% |
| | insufficiently compensated dysfunction, near life-threatening emergency, myocardial impairment, quadrants III/IV. |

TABLE 1

| | | N | P1 | P2 | P3 | P4 |
|---|---|---|---|---|---|---|
| EDVI | (ml/m$^2$) | 70.5 | 101 | 62 | 57 | 90 |
| ESVI | (ml/m$^2$) | 29.5 | 22 | 19 | 40 | 53 |
| SBP | (mm Hg) | 25 | 30 | 25 | 75 | 33 |
| EDP | (mm Hg) | 12 | 14 | 11 | 40 | 20 |
| HR | (1/min) | 60 | 67 | 70 | 90 | 65 |
| PEP | (Merg/m$^2$) | 1.2 | 2.1 | 1.2 | 2.7 | 1.6 |
| EDVI*SBP | (Merg/m$^2$) | 2.3 | 4.0 | 2.1 | 5.7 | 4.0 |
| EDVI*EDP | (Merg/m$^2$) | 1.1 | 1.9 | 0.9 | 3.0 | 2.4 |
| POP | (Merg/m$^2$) | 0.5 | 0.5 | 0.3 | 1.9 | 0.9 |
| ESVI*SBP | (Merg/m$^2$) | 1.0 | 0.9 | 0.6 | 4.0 | 2.3 |
| ESVI*EDP | (Merg/m$^2$) | 0.5 | 0.4 | 0.3 | 2.1 | 1.4 |
| W | (Merg/m$^2$) | 0.7 | 1.6 | 0.9 | 0.8 | 0.7 |
| W | (CMET) | 1.0 | 2.2 | 1.2 | 1.1 | 0.9 |
| CF | (%) | 30 | 40 | 43 | 14 | 18 |
| CP | (CMET/sec) | 1.0 | 2.5 | 1.4 | 1.7 | 1.0 |
| MCP | (CMET/sec) | 3.3 | 4.4 | 2.3 | 8.6 | 3.9 |
| EF(V) | (%) | 58 | 79 | 69 | 30 | 41 |
| EF(P) | (%) | 52 | 19 | 25 | 52 | 24 |

Figure 6A:
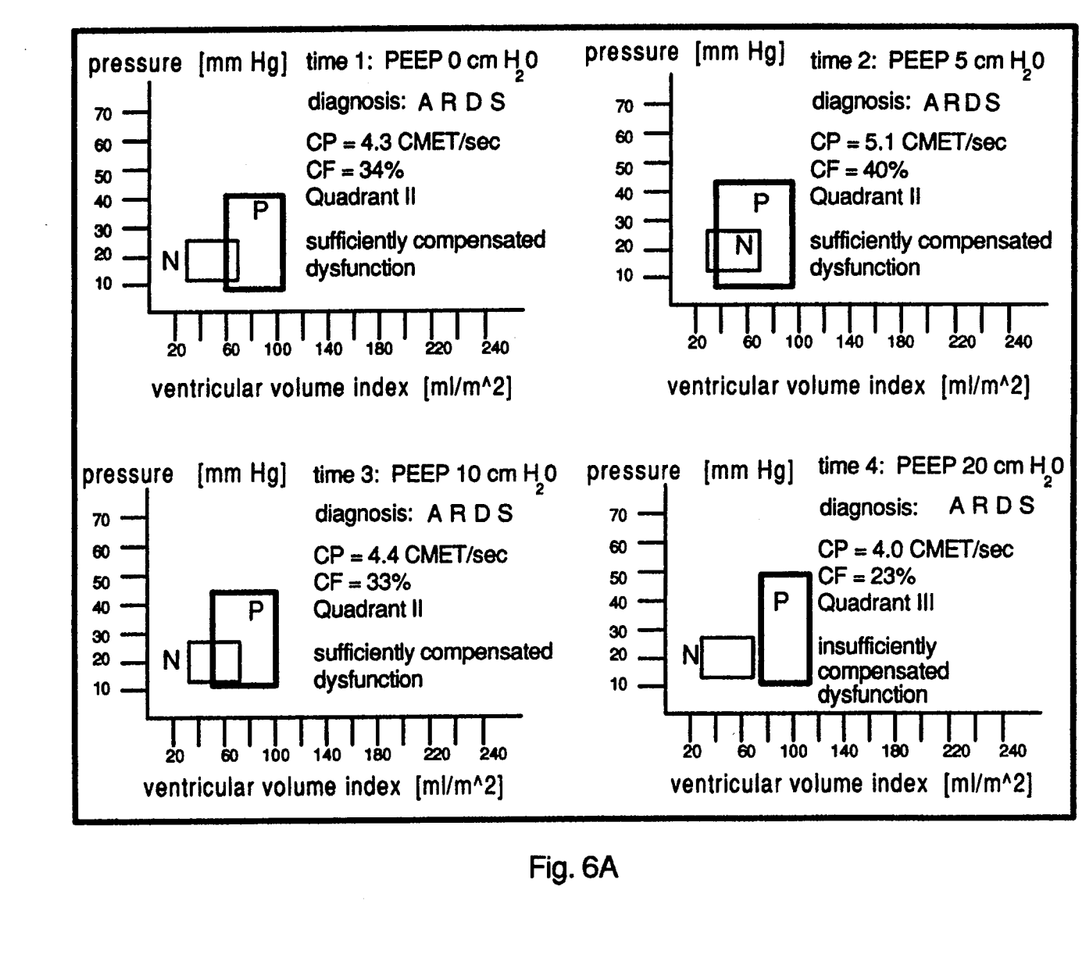
FIGS. 6A, 6B and 6C illustrate the utility of the present invention for diagnosing displaced incongruent areas of pressure-volume curves derived from measuring cardiac functioning, displaced pre-ejection potentials, displaced post-ejection potentials, myocardial impairments, dysfunctions sufficiencies, and insufficiencies.
Figure 6B:
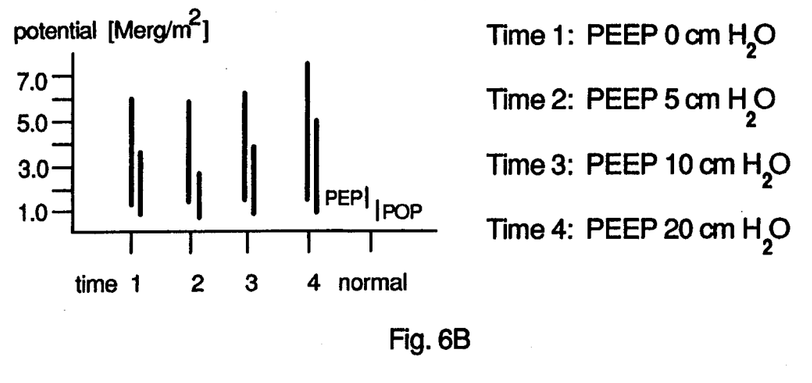
Figure 6C:
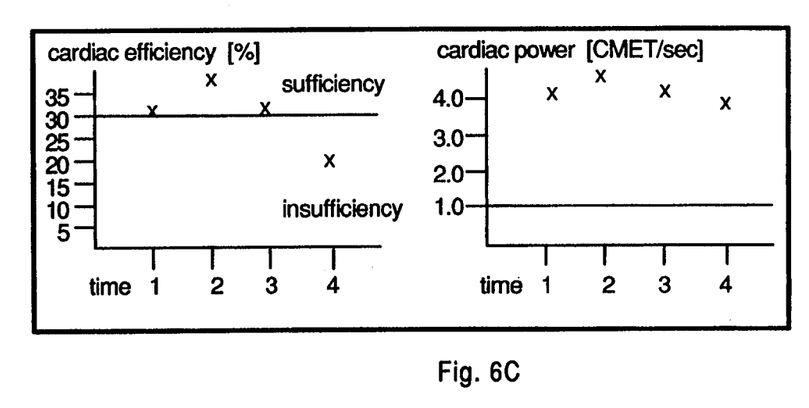

Referring now to FIGS. 6A, 6B and 6C, measured values of cardiac performance and other data published by Biondi et al. in a work entitled *The Effect of Positive End-expiratory Pressure on Right Ventricular Hemodynamic and Ejection Fraction*, Anesth. Analg. 1988; 67:144–151 was used to produce the ventricular pressure-volume curves displayed in FIG. 6A for a normal and for a patient at four different times (times 1, 2, 3 and 4) afflicted with the acute respiratory disease syndrome. These data were used to form plots of pre-ejection potentials and post-ejection potentials in FIG. 6B and in FIG. 6C to form the plots points of cardiac efficiency, and cardiac power. The various times 1, 2, 3 and 4 are representative of various positive end-expiratory pressures (PEEP) administered to the patient. Pressure-volume diagnosis reveals the displacement of the ventricular pressure-volume curve, the displacement of pre-ejection potential and post-ejection potential of the patient compared to the normal. CP>1 CMET/sec at all PEEPs indicative of the dysfunction acute respiratory disease syndrome. CF=40%, which is a maximum, for a PEEP of 5 cm H$_2$O and, thus, identifies the most beneficial PEEP treatment of this patient. No myocardial impairment or a sufficiently compensated dysfunction (respiratory disease) exists for all PEEP treatments except a PEEP of 20 cm H$_2$O suggesting that this pressure is detrimental to the patient's health. According to the instant invention an apparatus and method is disclosed in this particular embodiment to diagnose the degree of acute respiratory disease dysfunction and the absence of myocardial impairment (sufficiency) and the degree of myocardial impairment (insufficiency), if present, and to design and monitor patient-specific treatments via differential diagnosis to improve myocardial impairment to gain sufficiency and to minimize dysfunctions.

All hemodynamic parameters, in particular cardiac efficiency and contractility may be standardized with respect to cardiac basal metabolic rate. The hemodynamic parameters of the patient may be in real time or historical through the use of a storage unit in a computer.

The pictorial representation of cardiac efficiency diagnosis in form of ventricular pressure-size curves and pre-ejection potentials and post-ejection potentials displaced from the similar pre-determined curves of cardiac basal metabolic rate enables patient diagnosis and therapy development as a pictorial model. An analysis without the pictorial model is unreasonable, if not an impossible imposition on the human mind by the requirement to accumulate an understanding of the data including the various representative curves. Furthermore, the pictorial representation of cardiac sufficiency in form of a threshold of 1 CMET/sec which must be maintained to sustain life also contributes to simplification of diagnosis and therapy design.

Although the invention has been described within the context of the preferred embodiments with respect to the right heart, they also pertain to the left heart and many alterations, modifications, changes, and substitutions pertaining to left and right heart may be made by someone skilled in the art. While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

We claim:

1. A cardiac diagnostic and monitoring device for an individual including the combination of:

means for obtaining data representative of end-systolic size, end-diastolic size, ventricular systolic blood pressure, and ventricular end diastolic blood pressure;

means responsive to said means for obtaining data for generating electrical signals representative of cardiac ventricular sizes and ventricular pressures of said individual;

means responsive to said electrical signals for producing ventricular pressure-size curves;

means for pre-establishing ventricular pressure-size curves according to a pre-determined reference; and display means for said ventricular pressure-size curves to allow comparison with said pre-established curves of a pre-determined reference to allow diagnostic monitoring of the individual.

2. The device according to claim 1 further including means for generating electrical signals corresponding to said pre-established ventricular pressure-size curves, said display means being responsive to electrical signals representing ventricular pressure-size curves derived from the ventricular sizes and ventricular pressures of said individual and curves of the pre-determined reference by display in a coordinate frame of reference to allow said comparison.

3. The device according to claim 2 wherein said means for generating electrical signals includes an operating program to construct displays of the ventricular pressure-size curves representing said cardiac ventricular sizes and ventricular pressures and the ventricular pressure-size curves representing said pre-determined reference circumscribe areas within said frame of reference to allow assessment of displaced and incongruent pathological curves indicative of a degree of cardiac dysfunction.

4. The device according to claim 1 wherein said means for producing signals includes a pulmonary artery ejection fraction catheter having a thermistor.

5. The device according to claim 1 wherein said means for producing signals includes a echocardiographic instrumentation.

6. The device according to claim 1 wherein signals representative of body surface normalized values for end-diastolic size and end-systolic size for one cardiac cycle are produced by said means for generating signals.

7. The device according to claim 1 wherein said means responsive to said signals for producing pressure-size curves includes a programmed computer for generating electrical signals corresponding to said preestablished pressure-size curves.

8. A cardiac diagnostic and monitoring device for an individual including the combination of:
means for producing and detecting signals representative of cardiac ventricular sizes and ventricular pressures of said individual;
means responsive to said signals for generating energy level signals representing pre-ejection potentials and post-ejection potentials of said individual;
means for pre-establishing energy levels of pre-ejection and post-ejection potentials of a pre-determined reference; and
display means for said energy level signals representing pre-ejection and post-ejection potentials to allow comparison with said pre-established energy levels of pre-ejection and post-ejection potentials of a pre-determined reference to allow diagnosis and monitoring of the individual.

9. The device according to claim 8 further including means for generating electrical signals corresponding to said pre-established energy levels, said display means including means for display of energy levels representing pre-ejection and post-ejection potentials of said individual and electrical signals corresponding to said pre-established energy levels in an energy reference frame to allow said comparison.

10. The device according to claim 9 wherein said display means includes a display from wherein energy levels representing said pre-ejection potentials and post ejection potentials of said individual and the energy levels representing said pre-determined reference are displayed to allow assessment of energy level differences indicative of a degree of cardiac dysfunction.

11. The device according to claim 8 wherein said means for generating electrical signals uses said pre-established energy levels to generate a basal cardiac metabolic rate signal.

12. The device according to claim 8 wherein said means responsive to said signals generating energy level signals includes a programmed computer for generating electrical signals corresponding to such energy levels.

13. The device according to claim 8 wherein said means for generating energy level signals includes means for generating the cardiac efficiency signal for determining the presence or absence of myocardial impairment or sufficiency.

14. The device according to claim 13 wherein said means for generating energy level signals includes means for generating a signal corresponding to cardiac power for displaying a reference frame for determining a sufficiently compensated or insufficiently compensated dysfunction or life-threatening emergency.

15. The device according to claim 8 wherein said means for generating energy level signals includes means for generating a signal corresponding to maximum cardiac power and contractility for determining myocardial impairment and dysfunction.

16. The device according to claim 8 wherein said means for generating signals is further defined to include generating hemodynamic signals of an individual to establish ventricular pressure-size curves, pre-ejection and post-ejection potentials according to the expressions:

$PEP = EDVI * SBP - EDVI * EDP$;
$POP = ESVI * SBP - ESVI * EDP$;
$W = PEP - POP$;
$CF = (PEP - POP)/EDVI * SBP$; and
$CP = W/RR$;
$CON = m_1/(CF + EDP/SBP + ESVI/EDVI - 1)$
$MCP = EDVI * SBP/RR$
$EDVI = EDV/BSA$;
$ESVI = ESV/BSA$;

where PEP is pre-ejection potential;
EDV is end-diastolic size corresponding to either end-diastolic volume or end-diastolic cross-sectional area;
EDVI is end-diastolic size index;
SBP is systolic pressure;
ESV is end-systolic size corresponding to either end-systolic volume or end-systolic cross-sectional area;
ESVI is end-systolic size index;
EDP is end-diastolic pressure;
POP is post-ejection potential;
W is mechanical heart work;
CF is cardiac efficiency;
CP is cardiac power;
RR is time of one heart beat;
CON is the contractility;
MCP is the maximal cardiac power; and
wherein said display means display signals representing the pressure-size curve, pre-ejection potential/post-ejection potential, work, cardiac efficiency, cardiac power, and the identification of sufficiency, insufficiency, and dysfunctions.

17. The device according to claim 8 wherein said means responsive to said signals generates a signal corresponding to cardiac work for display by said display means.

18. The device according to claim 8 further including means for generating electrical signals corresponding to the predetermined values of cardiac power measured as 1 CMET/sec and exercise and dysfunctions measured as multiples of 1 CMET/sec.

19. The device according to claim 8 further including means for generating a signal representative of time for completion of a cardiac cycle, and wherein said means responsive to said signals responds to said signal representative of time for completion of one cardiac cycle and heart rate signals and said signals representing energy levels for generating a signal representative of cardiac power for display by said display means of cardiac sufficiency and insufficiency.

20. A method of diagnosing cardiac efficiency, metabolic rate and cardiac power comprising the steps of:
providing an individual with detectors responsive to cardiac functions;
generating cardiac ventricular pressure and size signals using said detectors to represent end-diastolic size, end-systolic size, end-diastolic pressure, systolic pressure, of the individual;
using said signals to establish present curves and present pre-ejection and post-ejection potentials of the individual,
determining the curve and an energy level of pre-ejection and post-ejection potentials with cardiac basal metabolic rate, and
comparing the pressure-volume curves and the pre-ejection and post-ejection potentials of the individual with the respective curve and energy levels of the pre-ejection and post-ejection potentials of a pre-determined reference to assess cardiac efficiency.

21. The method according to claim 20 including the further step of using said signals to establish pre-ejection and post-ejection potentials for the individual and using the values for pre-ejection and post-ejection potentials of the individual and pre-established reference values for pre-ejection and post-ejection potentials to establish a measure of cardiac work and cardiac efficiency; and
providing a signal corresponding to said cardiac work and cardiac efficiency for display.

22. The method according to claim 20 further including the steps of:
establishing a time for completion of one cardiac cycle; and
establishing a measure of cardiac power as a computation using said time for completing of one cardiac cycle and said cardiac ventricular pressure and size; and
establishing a power reference frame scale with multiple numbers of CMET/sec.

* * * * *